United States Patent [19]

Müllner et al.

[11] Patent Number: 5,223,635
[45] Date of Patent: Jun. 29, 1993

[54] PREPARATION OF ORGANIC COMPOUNDS USING AS A REACTANT AN ADDUCT OF ISOCYANIC ACID AND A TERTIARY AMINE OR AN ETHER

[75] Inventors: Martin Müllner, Traun; Gerhard Stern, Sonnberg; Erich Schulz, Ansfelden, all of Austria

[73] Assignee: Chemie Linz Gesellschaft m.b.H., Linz, Austria

[21] Appl. No.: 768,369

[22] Filed: Sep. 25, 1991

Related U.S. Application Data

[62] Division of Ser. No. 552,694, Jul. 12, 1990, Pat. No. 5,078,980.

[30] Foreign Application Priority Data

Jul. 28, 1989 [AT] Austria ............................ A1828/89
Jul. 28, 1989 [AT] Austria ............................ A1829/89

[51] Int. Cl.$^5$ ............................ C01C 3/00; C01C 3/14; C01B 21/12; C07C 265/02
[52] U.S. Cl. ...................................... 558/232; 560/24; 560/330; 560/336; 560/346; 564/32; 564/61; 564/62
[58] Field of Search ............... 564/32, 61, 62; 560/24, 560/330, 336, 346; 558/232

[56] References Cited

U.S. PATENT DOCUMENTS

| | | | |
|---|---|---|---|
| 3,752,880 | 8/1973 | Stamm et al. | 560/24 |
| 3,953,427 | 4/1976 | Matolcsy et al. | 558/232 |
| 4,377,530 | 3/1983 | Trenbeath et al. | 560/24 |
| 4,398,036 | 8/1983 | McCoy et al. | 560/24 |
| 5,078,980 | 1/1992 | Müllner et al. | 560/24 |
| 5,091,553 | 2/1992 | Müllner et al. | 560/24 |

FOREIGN PATENT DOCUMENTS

| | | | |
|---|---|---|---|
| 0124704A2 | 11/1984 | European Pat. Off. | 560/24 |
| 1204643 | 11/1965 | Fed. Rep. of Germany | 560/24 |
| 1373291 | 11/1974 | United Kingdom | 560/24 |

OTHER PUBLICATIONS

Chemical Abstracts, vol. 82, 173135u, p. 129 (1975).
Chemical Abstracts, vol. 81, 172444m, p. 178 (1974).
Beilsteins Handbuch Der Organischen Chemie, 4th Edition, vol. 3, p. 33, (1921).
Beilsteins Handbuch Der Organischen Chemie, 4th Edition, vol. 4, p. 101, (1922).
Noller, Lehrbuch der Organischen Chemie, Springer-Verlag, (1960), p. 330.

*Primary Examiner*—Floyd D. Higel
*Attorney, Agent, or Firm*—Wenderoth, Lind & Ponack

[57] ABSTRACT

Process for the removal of isocyanic acid from a gaseous mixture of isocyanic acid and ammonia by introducing a tertiary amine or ether at 250° to 600° C. The gaseous reaction mixture is passed into an inert diluent and cooled, to condense an adduct of isocyanic acid and tertiary amine or ether, and the ammonia being removed as a gas.

9 Claims, No Drawings

PREPARATION OF ORGANIC COMPOUNDS USING AS A REACTANT AN ADDUCT OF ISOCYANIC ACID AND A TERTIARY AMINE OR AN ETHER

This application is a divisional of Ser. No. 07/552,694 filed Jul. 12, 1990, now U.S. Pat. No. 5,078,980.

The invention relates to a process for the removal of isocyanic acid from a gaseous mixture of isocyanic acid and ammonia in the form of an adduct of isocyanic acid and tertiary amine or of isocyanic acid and ether.

Mixtures of isocyanic acid and ammonia are used, inter alia, as a starting material for the synthesis of melamine and are obtained by thermal decomposition of urea, for example according to EP-A-0,124,704.

Isocyanic acid itself would be a useful reactive C-1 building block for the synthesis of a large number of organic compounds. However, its use for this purpose is limited since it is not very stable and easily polymerizes to give linear and cyclic polymers. In addition, it can only be prepared in a complicated manner. Thus, in Chemical Abstracts, Vol.81 (1974) 172444m and Vol. 82 (1975), 173135u, the formation of isocyanic acid by thermal decomposition of urea with the removal of ammonia is described, in which case, however, a solid, namely cyanuric acid, is produced which must be decomposed at 330° to 600° C. to give isocyanic acid. It is known here that the decomposition of cyanuric acid only proceeds slowly and incompletely as cyanuric acid is very stable in comparison to isocyanic acid.

It has now been found that, in the separation of isocyanic acid from a gaseous mixture of isocyanic acid and ammonia, the roundabout route via the cyanuric acid can be avoided if a tertiary amine or an ether is added to the mixture of isocyanic acid and ammonia, and the gaseous reaction mixture formed is cooled and condensed. Unexpectedly, and in spite of the presence of ammonia in the reaction mixture, ammonium isocyanate is not formed here, but an adduct of isocyanic acid with the tertiary amine used in each case or the ether used in each case is formed. The ammonia remains gaseous and can be removed. In this case, the adducts of isocyanic acid and tertiary amine and the adducts of isocyanic acid and ether are more stable than free isocyanic acid. The adducts can be used for further reaction with various substrates.

The invention therefore relates to a process for the removal of isocyanic acid from a gaseous mixture of isocyanic acid and ammonia, which is characterized in that a tertiary amine or an ether is introduced into a gaseous mixture of isocyanic acid and ammonia at a temperature of 250° to 600° C. and the resulting gaseous reaction mixture is introduced into a diluent which is inert under the reaction conditions and cooled, to condense an adduct of isocyanic acid and tertiary amine or ether.

The mixture of isocyanic acid and ammonia needed to carry out the process according to the invention is prepared, for example, by decomposition of urea and is diluted, if desired, using a carrier gas such as nitrogen, argon or ammonia. A tertiary amine or an ether is then added to the mixture.

Suitable tertiary amines are, for example, tertiary cyclic amines such as N-alkylpyrrolidine, N-alkylpyrrole, N-alkylpiperidine, pyridine, N-alkylmorpholine or amines of the general formula $NR_1R_2R_3$, in which the radicals $R_1$, $R_2$ and $R_3$ independently of one another denote straight-chain or branched alkyl, aryl, alkylaryl or arylalkyl groups.

Suitable ethers are, for example, cyclic ethers, such as furan, pyran, tetrahydrofuran, dioxane or ethers of the general formula $R_1$—O—$(R_4$—O$)_n$—$R_2$ in which the radicals $R_1$ and $R_2$ have the abovementioned meaning and $R_4$ denotes a straight-chain or branched alkylene, arylene, alkylarylene or arylalkylene group and n denotes an integer from 0 to 5.

Straight-chain or branched alkyl groups are, for example, alkyl groups having 1 to 10 C atoms, such as methyl, ethyl, propyl or butyl groups and their isomers, such as iso-propyl, iso-butyl or tert. butyl groups. Aryl, alkylaryl or arylalkyl groups are phenyl groups which can be connected to the nitrogen atom or the ether oxygen atom either via an aromatic or via an aliphatic carbon atom and are optionally monosubstituted or polysubstituted by straight-chain or branched alkyl groups having 1 to 5 C atoms. Examples of such groups are, for example, phenyl, tolyl, dimethylphenyl, trimethylphenyl, ethylphenyl, isopropylphenyl, benzyl, methylbenzyl or ethylenephenyl groups. Alkylene groups are, for example, alkylene groups having 1–10 C atoms, such as methylene, ethylene, propylene or butylene groups and their isomers, such as iso-propylene, iso-butylene and tert.-butylene groups. Arylene, alkylarylene or arylalkylene groups are phenyl or phenylene groups which can be connected to the ether oxygen atom either via an aromatic or via an aliphatic carbon atom and which are optionally monosubstituted or polysubstituted by straight-chain or branched alkyl or alkylene groups having 1–5 C atoms. Examples of such groups are phenylene, methylphenylene, benzylene, dimethylphenylene, trimethylphenylene, ethylphenylene, iso-propylphenylene, methylbenzylene or ethylenephenyl groups.

Preferred tertiary amines are tertiary amines of the general formula $NR_1R_2R_3$ in which $R_1$, $R_2$ and $R_3$ are identical and denote an alkyl group. Particularly preferred here are alkyl groups having 1 to 5 C atoms, for example trimethylamine, triethylamine, tripropylamine, tributylamine and triisopentylamine. Trimethylamine, triethylamine and triisopentylamine are very particularly preferred.

Preferred ethers are ethers of the general formula $R_1$—O—$R_2$ in which $R_1$ and $R_2$ are identical and denote alkyl groups, or ethers of the formula $R_1$—O—$R_4$—O—$R_2$ in which $R_1$ and $R_2$ are identical and denote alkyl groups and $R_4$ denotes an alkylene group.

The tertiary amine or the ether is introduced into the hot gas mixture of isocyanic acid and ammonia in gas form if necessary by heating and, if desired, with the aid of a carrier gas, or in liquid form, by spraying in or dripping in, the tertiary amine or the ether, in this case first being converted into the gaseous state in the gas mixture by its high temperature.

It is possible to add the tertiary amine or the ether to the isocyanic acid here in approximately equimolar amounts, or to employ an excess of the tertiary amine or the ether. Preferably, 1 to 7 moles, particularly preferably 1.5 to 4 moles, of amine or ether are employed per mole of isocyanic acid. The temperature at which the tertiary amine or the ether is added to the gaseous mixture of isocyanic acid and ammonia is about 250° to 600° C., preferably 300° to 450° C., particularly preferably 320° to 380° C.

As a result of the addition of the tertiary amine or the ether to the gas mixture of isocyanic acid and ether, a hot gaseous reaction mixture is formed. The contact time of the gaseous reactants in the reaction mixture is in this case dependent on the size of the apparatus and the flow rate of the gases, a contact time of a few seconds in general being sufficient.

The resulting hot gaseous reaction mixture is then passed into a liquid inert diluent which has been introduced.

Suitable inert diluents are, for example, aliphatic hydrocarbons, such as pentane, hexane, heptane, aromatic hydrocarbons, such as benzene, toluene, xylene, halogenated aliphatic hydrocarbons, such as methylene chloride, chloroform, carbon tetrachloride, ethyl chloride, ethylene chloride, halogenated aromatic hydrocarbons, such as chlorobenzene, trichlorobenzene, carboxamides, such as dimethylformamide, N-methylpyrrolidone or ethers, such as diethyl ether, diisopropyl ether, dibutyl ether, ethyl methyl ether, dioxane, diethoxyethane, tetrahydrofuran or mixtures of the abovementioned diluents. Aromatic hydrocarbons, halogenated aliphatic hydrocarbons and carboxamides or ethers are preferred, and toluene, chloroform or N-methylpyrrolidone or the ether with which the formation of the adducts of isocyanic acid and ether takes place are particularly preferred. The ether is used here both as a reactant and as an inert diluent.

The hot gaseous reaction mixture is cooled on passing into the liquid inert diluent or the hot gaseous reaction mixture is precooled before passing it into the liquid inert diluent, for example with the aid of heat exchangers. The gaseous reaction mixture is introduced into the liquid inert diluent for example by passing in, or via packed columns, scrubbers, etc. The liquid inert diluent can be introduced in cooled form here, for example with the aid of heat exchangers.

The adduct of isocyanic acid and tertiary amine or of isocyanic acid and ether condenses in the diluent introduced, while the ammonia escapes in gaseous form. For the complete removal of the ammonia, an inert carrier gas such as nitrogen or argon can be blown through the solution or suspension formed.

In a preferred embodiment, gaseous trimethylamine, triethylamine, triisopentylamine or dioxane, diisopropyl ether, diphenyl ether or diethoxyethane is blown into the mixture of isocyanic acid and ammonia at temperatures of 320° to 380° C., after which the hot gas stream is brought into contact in a scrubber with cooled toluene, chloroform, N-methylpyrrolidone or dioxane, diisopropyl ether, diphenyl ether or diethoxyethane through which nitrogen is passed. The adduct condenses and the gaseous ammonia and any in dissolved form is removed with the aid of the nitrogen stream.

The process can be carried out continuously or batchwise, but is preferably carried out continuously.

Depending on the nature of the diluents used or depending on the nature of the adduct, a solution or a suspension of an adduct of isocyanic acid with a tertiary amine or of isocyanic acid with an ether is obtained in the manner described above, which can be used for further reaction with all sorts of substrates. It may be possible that the adduct exists dissolved in a suspension and a solid which is not an adduct is deposited. In such cases, the suspension is advantageously filtered before further use and removed from by-product formed. If an ether/isocyanic acid adduct has been produced, purification by distillation can be carried out if desired.

By reaction of the adduct in a diluent which is inert under the reaction conditions and at temperatures of −20° C. up to the boiling point of the diluent used, an asymmetrically substituted urea is obtained using a primary or secondary amine, a carbamate is obtained using an alcohol, a thiocarbamate is obtained using a thiol, and a substituted isocyanate is obtained using a compound which contains one or two non-cumulated olefinic double bonds.

EXAMPLE 1

100 g of urea per hour were introduced continuously into a decomposer. The pyrolysis gases were caused to react in a heatable tube at 320° C. with 255 g of triethylamine per hour which was introduced in gaseous form. Altogether 213 g of urea (3.5 mol) and 544 g of triethylamine (5.4 mol) were introduced. The reaction gases were rapidly cooled to room temperature in a scrubber which was operated with chloroform which was cooled to −10° C. The organic phase was filtered.

66% of theory of an adduct of isocyanic acid and triethylamine, dissolved in chloroform, were obtained in this way.

IR: 2160 cm$^{-1}$ (N=C=O), sharp band.

The adduct content of the solution was determined by acid hydrolysis and determination of the escaping $CO_2$ with the aid of barium hydroxide solution.

EXAMPLE 2

60 g of urea per hour were continuously introduced into a decomposer. The pyrolysis gases were caused to react in a heatable tube at 320° C. with 285 g of triethylamine per hour which was introduced in gaseous form. Altogether 71 g of urea (1.2 mol) and 388 g of triethylamine (3.3 mol) were introduced.

The reaction gases were rapidly cooled to room temperature in a scrubber which was operated with toluene.

55% of theory of an adduct of isocyanic acid and triethylamine, suspended in toluene, were obtained in this way. The yield was determined as described in Example 1.

IR: 2160 cm$^{-1}$ (N=C=O), sharp band.

EXAMPLE 3

As described in Example 1, but using 100 g of urea (1.7 mol), 200 g of triethylamine (1.98 mol) and N-methylpyrrolidone which was cooled to −10° C. as the diluent, 62% of theory of an adduct of isocyanic acid and triethylamine was obtained.

IR: 2160 cm$^{-1}$ (N=C=O), sharp band.

EXAMPLE 4

As described in Example 1, but using 80 g of urea (1.3 mol), 160 g of triethylamine (1.58 mol) and n-hexane which was cooled to −20° C. as the diluent, 52% of theory of an adduct of isocyanic acid and triethylamine was obtained.

IR: 2160 cm$^{-1}$ (N=C=O), sharp band.

EXAMPLE 5

As described in Example 1, but using 252.2 g of urea (4.2 mol) and 796 g of triisopenylamine (3.5 mol), 50% of theory of an adduct of isocyanic acid and triisopentylamine was obtained after filtering the resulting suspension.

IR: 2160 cm$^{-1}$ (N=C=O), sharp band.

EXAMPLE 6

As described in Example 2, but using 305 g of N,N-dimethylcyclohexylamine (2.4 mol) and chloroform at a temperature of −10° C. as the diluent; 62% of theory of an adduct of isocyanic acid and N,N-dimethylcyclohexylamine, dissolved in chloroform, was obtained after filtering the resulting suspension.

IR: 2160 cm$^{-1}$, (N=C=O), sharp band.

EXAMPLE 7

As described in Example 1, but using 71 g of urea (1.2 mol) and 238 g of N-methylpiperidine (2.4 mol) and chloroform which was cooled to −10° C. as the diluent, 51% of theory of an adduct of isocyanic acid and N-methylpiperidine, dissolved in chloroform, was obtained.

IR: 2160 cm$^{-1}$ (N=C=O) sharp band.

EXAMPLE 8

90 g of urea per hour were continuously introduced into a decomposer. The pyrolysis gases were caused to react in a heatable tube at 360° C. with 372 g of N,N-dimethylaniline per hour which was introduced in gaseous form with the aid of a stream of nitrogen. Altogether 135 g of urea (2.3 mol) and 557 g of N,N-dimethylaniline (4.6 mol) were introduced. The reaction gases were rapidly cooled in a scrubber which was operated with chloroform and cooled to −15° C. The resulting suspension was filtered. 58% of theory of an adduct of isocyanic acid and N,N-dimethylthylaniline, dissolved in chloroform, was obtained in this way. The yield was determined as described in Example 1.

IR: 2160 cm$^{-1}$ (N=C=O), sharp band.

EXAMPLE 9

80 g of urea per hour were continuously introduced into a decomposer. The pyrolysis gases were caused to react in a heatable tube at 340° C. with 217 g of N-benzyldimethylamine per hour which was introduced in gaseous form with the aid of nitrogen.

Altogether 96.1 g of urea (1.6 mol) and 242 g of N-benzyldimethylamine (2.0 mol) were introduced.

The reaction gases were cooled in a scrubber which was operated with chloroform which was cooled to −15° C. The resulting suspension was filtered. 61% of theory of an adduct of isocyanic acid and N-benzyldimethylamine, dissolved in chloroform, was obtained in this way. The yield was determined as described in Example 1.

IR: 2160 cm$^{-1}$ (N=C=O), sharp band.

EXAMPLE 10

80 g of urea per hour were continuously introduced into a decomposer. The pyrolysis gases were caused to react in a heated tube at 360° C. with 120 g of gaseous dioxane per hour. Altogether 400 g of urea (6.66 mol) and 600 g of dioxane (6.81 mol) were employed. The reaction gases were cooled in a scrubber operated with dioxane at 10° C. The resulting dissolved adduct was filtered off from a precipitated solid.

1700 g of a solution was obtained in this way which was 24% strength in isocyanic acid/dioxane adduct, which corresponds to a yield of 47% of theory. The yield was determined as described in Example 1.

IR: 2160 cm$^{-1}$ (N=C=O), sharp band.

EXAMPLE 11

80 g of urea per hour were continuously introduced into a decomposer. The pyrolysis gases were caused to react in a heated tube at 350° C. with 306 g of gaseous diisopropyl ether per hour. Altogether 160 g of urea (2.66 mol) and 612 g of diisopropyl ether (5.99 mol) were employed. The reaction gases were cooled in a scrubber at 10° C. operated with diisopropyl ether. The resulting dissolved adduct was filtered off from a precipitated solid. 1700 g of a solution were obtained in this way which was 15% strength in isocyanic acid/diisopropyl ether adduct, which corresponds to a yield of 70% of theory. The yield was determined as described in Example 1.

IR: 2160 cm$^{-1}$ (N=C=O), sharp band.

EXAMPLE 12

40 g of urea per hour were continuously introduced into a decomposer. The pyrolysis gases were caused to react in a heated tube at 370° C. with 113 g of gaseous diphenyl ether per hour. Altogether 160 g of urea (2.66 mol) and 452 g of diphenyl ether (3.51 mol) were employed. The reaction gases were cooled in a scrubber at 10° C. operated with chloroform. The resulting suspension was filtered off from a precipitated solid.

2000 g of a solution were obtained in this way which was 17% strength in isocyanic acid/diphenyl ether adduct, which corresponds to a yield of 60% of theory. The yield was determined as described in Example 1.

IR: 2160 cm$^{-1}$ (N=C=O), sharp band.

EXAMPLE 13

120 g of urea per hour were continuously introduced into a decomposer. The pyrolysis gases were caused to react in a heated tube at 380° C. with 350 g of gaseous diethoxyethane per hour. Altogether 120 g (2 mol) of urea and 350 g (3 mol) of diethoxyethane were employed. The reaction gases were cooled rapidly in a scrubber at 10° C. operated with diethoxyethane.

The solution of the isocyanic acid/diethoxyethane adduct in diethoxyethane was then distilled. 270 ml of a fraction were obtained in the distillation under normal pressure between 70° and 110° C. which was 74% strength in isocyanic acid/diethoxyethane adduct, which corresponds to 62% of theory. The yield was determined as described in Example 1.

IR: 2160 cm$^{-1}$ (N=C=O), sharp band.

EXAMPLE 14

14.1 g of dodecylamine (0.076 mol) dissolved in 20 ml of chloroform were added dropwise at room temperature with stirring to 100 ml of a solution of 10 g of triethylammonium isocyanate (0.069 mol) in chloroform, prepared according to Example 1. After completion of the addition the mixture was subsequently stirred at room temperature for 24 hours and heated to reflux for 1 hour. The solvent was evaporated and the residue was recrystallized from chloroform. 9.45 g, i.e. 60% of theory, of dodecylurea were obtained in this way.

C—H—N analysis:
theoretical: C 68.4%, H 12.3%, N 12.3%;
found: C 68.2%, H 12.3%, N 12.3%.

EXAMPLE 15

6.7 g (0.146 mol) of ethanol were added dropwise at room temperature with stirring to 100 ml of a solution of 10.5 g (0.073 mol) of triethylammonium isocyanate in chloroform, prepared according to Example 1, after which the mixture was subsequently stirred at room temperature for 24 hours and then heated to reflux for 1 hour.

The solvent was evaporated and the residue was recrystallized from ethanol, 4.6 g, i.e. 71% of theory, of ethyl carbamate having a melting point of 46°-50° C. being obtained.

EXAMPLE 16

18.5 g (0.3 mol) of ethylmercaptan, dissolved in 30 ml of chloroform, was added dropwise at 0° C. with stirring to 120 ml of a solution of 28 g (0.2 mol) of triethylammonium isocyanate in chloroform, prepared according to Example 1, after which the mixture was subsequently stirred at this temperature for a further hour and then at room temperature for 15 hours. After this, the reaction mixture was heated under reflux for 2 hours. The solvent was then distilled off. The oily residue remaining crystallized on cooling and was recrystallized from water.

16 g (0.15 mol), i.e. 75% of theory, of S-ethyl thiocarbamate having a melting point of 99°-102° C. were obtained in this way.

EXAMPLE 17

3 g (0.025 mol) of alpha-methylstyrene were added dropwise with stirring to 100 ml of a suspension of 11.3 g (0.078 mol) of triethylammonium isocyanate in toluene, after which the mixture was subsequently stirred at room temperature for 3 hours and then heated to reflux for about 4 hours.

A solution of alpha,alpha-dimethylbenzyl isocyanate in toluene was obtained in this way.

After distillation at 40° to 45° C., 1 Torr, alpha,alpha-dimethylbenzyl isocyanate having an $n_D^{25}$ of 1.5048 was obtained in a yield of 55% of theory.

What we claim is:

1. A process for the preparation of asymmetrically substituted ureas, carbamates, thiocarbamates or substituted isocyanates, comprising:
   providing an adduct of isocyanic acid and a tertiary amine or an ether, prepared by a process which comprises introducing a tertiary amine or an ether into a gaseous mixture of isocyanic acid and ammonia at a temperature of 250° to 600° C., introducing the resulting gaseous reaction mixture into a diluent which is inert under the reaction conditions, and cooling the reaction mixture whereby an adduct of isocyanic acid and tertiary amine or ether condenses, and
   reacting the adduct in an inert diluent at temperatures of $-20°$ C. up to the boiling point of the diluent, with a primary or secondary amine to give asymmetrically substituted ureas, an alcohol to give carbamates, a thiol to give thiocarbamates, or a compound which contains one or two noncumulated olefinic double bonds to give substituted isocyanates.

2. The process according to claim 1, wherein the tertiary amine is a tertiary cyclic amine or an amine of the general formula $NR_1R_2R_3$ in which the radicals $R_1$, $R_2$ and $R_3$ independently of one another denote straight-chain or branched alkyl, aryl, alkylaryl or arylalkyl groups.

3. The process according to claim 2, wherein the tertiary amine is a trialkylamine.

4. The process according to claim 1, comprising employing a cyclic ether or an ether of the general formula $R_1-O-(R_4-O)_n-R_2$ in which the radicals $R_1$ and $R_2$ independently of one another denote a straight-chain or branched alkyl, aryl, alkylaryl or arylalkyl group, $R_4$ denotes a straight-chain or branched alkylene, arylene, alkylarylene or arylalkylene group and n denotes an integer from 0 to 5.

5. The process according to claim 1, comprising employing an ether of the formula $R_1-O-R_2$ in which $R_1$ and $R_2$ are identical and denote alkyl groups, or an ether of the formula $R_1-O-R_4-O-R_2$ in which $R_1$ and $R_2$ have the above-mentioned meaning and $R_4$ denotes an alkylene group.

6. The process according to one of claims 1, 2, 3, 4, comprising introducing 1 to 7 moles of tertiary amine or ether per mole of isocyanic acid.

7. The process according to one of claims 4 or 5, comprising carrying out the addition of the tertiary amine or the ether at a temperature of 320° C. to 380° C.

8. The process according to one of claims 1, 2, 3, 4, comprising employing an optionally halogenated aliphatic or aromatic hydrocarbon, an ether, a carboxamide or a mixture of the abovementioned diluents as the diluent.

9. The process according to one of claims 4 or 5, comprising employing the ether which also forms the adduct of isocyanic acid and ether as the diluent.

* * * * *